(12) United States Patent
Bando et al.

(10) Patent No.: US 9,278,934 B2
(45) Date of Patent: Mar. 8, 2016

(54) METHOD FOR PRODUCING FINE PARTICLES OF ARIPIPRAZOLE ANHYDRIDE CRYSTALS B

(75) Inventors: Takuji Bando, Osaka (JP); Katsuhiko Yano, Osaka (JP); Makoto Fukana, Osaka (JP); Satoshi Aoki, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/128,305

(22) PCT Filed: Jun. 29, 2012

(86) PCT No.: PCT/JP2012/067258
§ 371 (c)(1),
(2), (4) Date: Jan. 30, 2014

(87) PCT Pub. No.: WO2013/002420
PCT Pub. Date: Jan. 3, 2013

(65) Prior Publication Data
US 2014/0228567 A1 Aug. 14, 2014

Related U.S. Application Data

(60) Provisional application No. 61/502,417, filed on Jun. 29, 2011.

(51) Int. Cl.
*C07D 401/12* (2006.01)
*C07D 403/02* (2006.01)
*C07D 215/22* (2006.01)

(52) U.S. Cl.
CPC .................... *C07D 215/22* (2013.01)

(58) Field of Classification Search
CPC .......................... C07D 401/12; C07D 403/02
USPC ......................................... 544/363; 514/253
See application file for complete search history.

(56) References Cited

U.S. PATENT DOCUMENTS

| | | | |
|---|---|---|---|
| 4,734,416 A | 3/1988 | Banno et al. | |
| 5,006,528 A | 4/1991 | Oshiro et al. | |

FOREIGN PATENT DOCUMENTS

| | | |
|---|---|---|
| CN | 102 060 763 A | 5/2011 |
| IN | 1946 CHE 2009 A1 | 8/2009 |
| JP | 2003-212852 | 7/2003 |
| WO | WO 03/026659 A1 | 4/2003 |
| WO | WO 2006/053780 A1 | 5/2006 |
| WO | WO 2006/053781 A1 | 5/2006 |

OTHER PUBLICATIONS

L. Tessler et al., "Crystal Structures of Aripiprazole, a New Antipsychotic Drug, and of Its Inclusion Compounds with Methanol, Ethanol and Water", Journal of Inclusion Phenomena and Macrocyclic Chemistry, vol. 55, pp. 255-261 (2006).
International Search Report from the European Patent Office for International Application No. PCT/JP2012/067258 mailed Oct. 10, 2012.
Written Opinion of the International Search Authority for International Application No. PCT/JP2012/067258 mailed Oct. 10, 2012.

*Primary Examiner* — James O Wilson
*Assistant Examiner* — Ebenezer O Sackey
(74) *Attorney, Agent, or Firm* — Finnegan, Henderson, Farabow, Garrett & Dunner, L.L.P.

(57) ABSTRACT

The present invention provides a novel method for producing fine particles of aripiprazole anhydride crystals B. The method for producing fine particles of aripiprazole anhydride crystals B comprises the steps of: (1) heating and dissolving crude aripiprazole in a lower alcohol, and subsequently cooling the resulting mixture to precipitate crystals to obtain crystals of aripiprazole lower alcohol solvate; (2) subjecting the crystals of aripiprazole lower alcohol solvate to wet-milling in the form of a slurry containing the lower alcohol; and (3) subjecting the dispersion of the wet-milled crystals to solid-liquid separation to obtain the crystals, and heating the crystals.

10 Claims, No Drawings

METHOD FOR PRODUCING FINE PARTICLES OF ARIPIPRAZOLE ANHYDRIDE CRYSTALS B

TECHNICAL FIELD

The present invention relates to a novel method for producing fine particles of aripiprazole anhydride crystals B.

BACKGROUND ART

Aripiprazole, i.e., 7-{4-[4-(2,3-dichlorophenyl)-1-piperazinyl]butoxy}-3,4-dihydrocarbostyril or 7-{4-[4-(2,3-dichlorophenyl)-1-piperazinyl]butoxy}-3,4-dihydro-2(1H)-quinolinone, is an antipsychotic drug useful in the treatment of schizophrenia and the like (Patent Literature 1 and Patent Literature 2).

Aripiprazole takes various forms, and is known to be present in monohydrate form (aripiprazole hydrate A) and other numerous anhydrous forms, i.e., anhydride crystals B, anhydride crystals C, anhydride crystals D, anhydride crystals E, anhydride crystals F, and anhydride crystals G.

Aripiprazole has been provided as a pharmaceutical product in the form of fine particles of anhydride crystals B.

When aripiprazole anhydride crystals B are used in the form of particles having a small particle size (less than 50 μm), anhydride crystals B having a large particle size must be milled. However, direct milling of anhydride crystals B has a problem such that milled drugs adhere to each other in the milling device. Therefore, it was difficult to produce aripiprazole anhydride crystals B having a small particle size on the industrial level (see Patent Literature 3, paragraph [0249]).

In order to solve this problem, it was found that aripiprazole anhydride crystals B having a small particle size can be prepared in the following manner: crude aripiprazole is crystallized in hydrous ethanol (water content is 20 vol %) to first prepare aripiprazole hydrate crystals A that can be easily milled; the thus-prepared hydrate crystals A are dry-milled (using a small atomizer) to obtain a fine particle size (20 to 25 μm); and the resulting product is heated at 90 to 125° C. (see Patent Literature 3, paragraphs [0250] to [0251]; Reference Examples 1 and 2; and Examples 1 to 4).

However, the above method for producing aripiprazole anhydride crystals B requires a multi-stage process, i.e., first obtaining aripiprazole hydrate crystals A; dry-milling the same; and further heating the same. Therefore, there has been a desire for an even shorter process in terms of cost and labor.

Patent Literature 4 discloses the crystalline form of alcohol solvates of aripiprazole (methanolate and ethanolate), and states that solvent-free aripiprazole crystals B can be prepared from alcohol solvates. However, Patent Literature 4 nowhere teaches the preparation of aripiprazole anhydride crystals B in the form of fine particles (average particle size of less than 50 μm), which is a desirable form for pharmaceutical products.

Rather, Patent Literature 4 (page 6, lines 1 to 7) states that hemiethanolates of aripiprazole are unstable for milling, and that the product resulting from milling does not have a form of any known solvent-free aripiprazole: it may be a mixture of Forms B and E, or a new form. In other words, Patent Literature 4 suggests that milling of a hemiethanolate of aripiprazole into fine particles causes contamination; and that, as a result, fine particles of high-purity, solvent-free aripiprazole crystals B cannot be obtained.

Under such a situation, there has been a strong demand for a method for efficiently preparing high-purity aripiprazole anhydride crystals B in the form of fine particles in a short process on an industrial scale.

CITATION LIST

Patent Literature

PLT 1: U.S. Pat. No. 4,734,416
PLT 2: U.S. Pat. No. 5,006,528
PLT 3: Japanese Unexamined Patent Publication No. 2003-212852
PLT 4: WO 2006/053780

SUMMARY OF THE INVENTION

Technical Problem

An object of the present invention is to provide a novel method for producing fine particles of aripiprazole anhydride crystals B. Specifically, the present invention aims to provide a method for efficiently producing fine particles of high-purity aripiprazole anhydride crystals B in a short process.

Solution to Problem

The present inventors conducted extensive studies to solve the above-described problem, and as a result, found that fine particles of aripiprazole anhydride crystals B can be easily and efficiently produced in the following manner: crude aripiprazole is recrystallized in an ethanol; precipitated hemiethanolate (½ ethanolate) of aripiprazole is subjected to wet-milling in the recrystallization solvent to obtain hemiethanolate crystals of aripiprazole in the form of fine particles (15 to 20 μm); and the crystals are heated (dried). The present invention was completed as a result of further examination based on the above finding.

The present invention provides the following method for producing fine particles of aripiprazole anhydride crystals B.

Item 1. A method for producing fine particles of aripiprazole anhydride crystals B, the method comprising the steps of:
(a) heating and dissolving crude aripiprazole in a lower alcohol, and subsequently cooling the resulting mixture to precipitate crystals to obtain crystals of aripiprazole lower alcohol solvate (e.g. methanolate, ethanolate);
(b) subjecting the crystals of aripiprazole lower alcohol solvate to wet-milling in the form of a slurry containing the lower alcohol; and
(c) subjecting the dispersion of the wet-milled crystals to solid-liquid separation to obtain the crystals, and heating the crystals.

Item 2. The production method according to Item 1, wherein the volume average particle size of the obtained fine particles of aripiprazole anhydride crystals B is less than 50 μm (preferably 5 to 40 μm, more preferably 10 to 30 μm, still more preferably 10 to 25 μm, and particularly preferably 15 to 20 μm).

Item 3. The production method according to Item 1 or 2, wherein the lower alcohol is methanol or ethanol.

Item 4. The production method according to any one of Items 1 to 3, wherein the lower alcohol is ethanol.

Item 5. The production method according to any one of Items 1 to 4, wherein the lower alcohol substantially contains no water.

Item 6. The production method according to any one of Items 1 to 5, wherein the water content in the lower alcohol is less than 10 vol % (preferably less than 5 vol %, more preferably less than 3 vol %, still more preferably less than 2 vol %, and particularly preferably less than 1 vol %).

Item 7. The production method according to any one of Items 1 to 6, wherein the volume average particle size of the wet-milled crystals in step (b) is less than 50 μm (preferably 5 to 40 μm, more preferably 10 to 30 μm, still more preferably 10 to 25 μm, and particularly preferably 15 to 20 μm).

Item 8. The production method according to Item 7, wherein the volume average particle size of the wet-milled crystals in step (b) is 15 to 20 μm.

Item 9. The production method according to any one of Items 1 to 8, wherein the heating temperature in step (c) is in the range near the boiling point of the lower alcohol to about 125° C.

Item 10. The production method according to any one of Items 1 to 9, wherein the lower alcohol is ethanol, and the heating temperature in step (c) is in the range of about 78 to 125° C.

Item 11. A method for producing fine particles of aripiprazole anhydride crystals B, the method comprising the steps of:
(b) subjecting crystals of aripiprazole lower alcohol solvate to wet-milling in the form of a slurry containing the lower alcohol; and
(c) subjecting the dispersion of the wet-milled crystals to solid-liquid separation to obtain the crystals, and heating the crystals.

Advantageous Effects of Invention

According to the production method of the present invention, fine particles of high-purity aripiprazole anhydride crystals B can be simply and efficiently produced. Particularly because high-purity aripiprazole anhydride crystals B in the form of fine particles, which is a desirable pharmaceutical form, can be efficiently produced in a short process, the present method is extremely useful as a production method on an industrial scale.

DESCRIPTION OF EMBODIMENTS

The present invention is described in detail below.

1. Aripiprazole Anhydride Crystals B

The aripiprazole anhydride crystals B contemplated by the present invention have the physicochemical properties (1) to (5) shown below.

(1) The crystals have characteristic peaks in a $^1$H-NMR spectrum (DMSO-$d_6$, TMS) at δ 1.55 to 1.63 ppm (m, 2H), 1.68 to 1.78 ppm (m, 2H), 2.35 to 2.46 ppm (m, 4H), 2.48 to 2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1 H), 7.04 ppm (d, J=8.1 Hz, 1 H), 7.11 to 7.17 ppm (m, 1H), 7.28 to 7.32 ppm (m, 2H), and 10.00 ppm (s, 1H). The present invention also encompasses crystals having a $^1$H-NMR spectrum that is substantially the same as the $^1$H-NMR spectrum described above.

(2) The crystals have characteristic peaks in a powder X-ray diffraction spectrum at 2θ=11.0°, 16.6°, 19.3°, 20.3°, and 22.1°. The present invention also encompasses crystals having a powder X-ray diffraction spectrum that is substantially the same as the powder X-ray diffraction spectrum described above.

(3) The crystals have significant infrared absorption bands in an IR (KBr) spectrum at 2945, 2812, 1678, 1627, 1448, 1377, 1173, 960, and 779 cm$^{-1}$. The present invention also encompasses crystals having an IR spectrum that is substantially the same as the IR (KBr) spectrum described above.

(4) The crystals show an endothermic peak near about 141.5° C. in thermogravimetric/differential thermal analysis (rate of temperature increase: 5° C./minute).

(5) The crystals show an endothermic peak near about 140.7° C. in differential scanning calorimetry (rate of temperature increase: 5° C./minute).

Aripiprazole anhydride crystals B have a low hygroscopicity; and, for example, maintain a water content of 0.4% or less, and further 0.1% or less, after 24 hours of conditioning in a desiccator set at a temperature of 60° C. and a humidity of 100%. Known methods for measuring water content can be used as long as they are commonly used for measuring the water content of crystals. For example, a method such as the Karl Fischer method can be used.

2. Method for Producing Fine Particles of Aripiprazole Anhydride Crystals B

Fine particles of aripiprazole anhydride crystals B can be produced, for example, in the following manner.

Crude aripiprazole used in the production method of the present invention can be prepared following or in accordance with the method described, for example, in Reference Example 1 in Patent Literature 3.

(a) Production of Crystals of Aripiprazole Lower Alcohol Solvate

The obtained crude aripiprazole is recrystallized in a lower alcohol so as to obtain crystals of aripiprazole lower alcohol solvate. Specifically, the crude aripiprazole is heated and dissolved in a lower alcohol, and the resulting product is subsequently cooled to precipitate crystals, thereby obtaining crystals of aripiprazole lower alcohol solvate. The heating temperature is usually 50° C. to near the boiling point of the lower alcohol, and it is particularly preferable to dissolve the crude aripiprazole by refluxing the lower alcohol. The cooling temperature is usually about 0 to 20° C., and particularly preferably about 5 to 15° C.

As the lower alcohol, methanol or ethanol is used. Ethanol is preferable, considering biological safety after administration.

In this step, in order to inhibit the production of a hydrate of aripiprazole, the lower alcohol used is preferably a lower alcohol that substantially contains no water. The phrase "substantially contains no water" used herein means that the water content is less than 10 vol %, preferably less than 5 vol %, more preferably less than 3 vol %, still more preferably less than 2 vol %, and particularly preferably less than 1 vol %. In other words, the lower alcohol content is 90 vol % or more, preferably 95 vol % or more, still more preferably 97 vol % or more, still yet more preferably 98 vol %, and particularly preferably 99 vol % or more.

Recrystallization using methanol as a lower alcohol usually results in the preparation of a monomethanolate of aripiprazole, while recrystallization using ethanol usually results in the preparation of a hemiethanolate (½ ethanolate) of aripiprazole.

(b) Wet-Milling

The thus-obtained aripiprazole lower alcohol solvate is subjected to wet-milling, in the form of slurry containing the lower alcohol. The recrystallized slurry in which the crystals of aripiprazole lower alcohol solvate are dispersed in the lower alcohol can be subjected to wet-milling as is; or, the slurry can also be subjected to wet-milling by increasing or decreasing the amount of lower alcohol, if necessary.

By the above-described wet-milling, the crystals of aripiprazole lower alcohol solvate are milled in the lower alcohol without being separated from the recrystallized slurry. Therefore, this method is advantageous in that it not only simplifies the process, but can also convert the crystals of aripiprazole lower alcohol solvate into fine particles while maintaining a high purity.

By wet-milling, the crystals of aripiprazole lower alcohol solvate are processed into fine particles. The volume average particle size after milling is less than 50 μm, preferably 5 to 40 μm, more preferably 10 to 30 μm, still more preferably 10 to 25 μm, and particularly preferably 15 to 20 μm.

The wet-type mill to be used is not particularly limited. Examples thereof include rotor-stator stirrers such as colloid mills, cone mills, ULTRA-TURRAX (produced by IKA Japan K.K.), T.K. Auto Homomixer (produced by PRIMIX Corporation), T.K. Pipeline Homomixer (produced by PRIMIX Corporation), T.K. Filmix (produced by PRIMIX Corporation),T.K. Robomix (produced by PRIMIX Corporation), CLEARMIX (produced by M Technique Co., Ltd.), CLEAR SS5 (produced by M Technique Co., Ltd.), Cavitron (produced by Eurotech Ltd.), and Fine Flow Mill (produced by Pacific Machinery & Engineering Co., Ltd.); media stirrers such as Viscomill (produced by Aimex Co., Ltd.), Apex Mill (produced by Kotobuki Industries Co., Ltd.), Star Mill (produced by Ashizawa Finetech Ltd.), DCP Superflow (produced by Nippon Eirich Co., Ltd.), MP Mill (produced by Inoue MFG., INC.), Spike Mill (produced by Inoue MFG., INC.), Mighty Mill (produced by Inoue MFG., INC.), and SC Mill (produced by Mitsui Mining Co., Ltd.); ultrasonic homogenizers; and the like.

Typically, CLEARMIX W-Motion (produced by M Technique Co., Ltd.) or the like is used for circulating and grinding for 10 to 40 minutes at a rotor speed of 15,000 to 22,000 rpm and a screen speed of 15,000 to 20,000 rpm.

The temperature during wet-milling is usually about 5 to 60° C., preferably 15 to 25° C. When heat is produced during milling, a cooling medium such as ice water or the like can be suitably used for cooling so that the temperature of the slurry is within the above-described ranges.

The volume average particle size is measured using a laser diffraction/scattering particle size distribution analyzer. For example, LMS-2000e produced by Seishin Enterprise Co., Ltd.; SALD-2200 produced by Shimadzu Corporation; and the like are used.

(c) Heating Treatment of the Crystals

The dispersion (circulated liquid or slurry) of the wet-milled crystals is subjected to solid-liquid separation to obtain the crystals; and the crystals are heated, thereby obtaining fine particles of aripiprazole anhydride crystals B. A common separation method such as filtration can be used as the solid-liquid separation method. The temperature of the heating treatment (drying) can be selected in the range near the boiling point of the lower alcohol (methanol or ethanol) to about 125° C. Typically, when ethanol is used as the lower alcohol, the temperature is usually about 78 to 125° C., and preferably 79 to 120° C. The heating time is usually about 10 to 50 hours.

By heretofore known methods for producing fine particles of aripiprazole anhydride crystals B (see Patent Literature 3), aripiprazole hydrate crystals A that were milled first are heated at a relatively high temperature (90 to 125° C.) to produce fine particles of aripiprazole anhydride crystals B. However, by the use of the method of the present invention, heating can be performed at a relatively moderate temperature because an aripiprazole lower alcohol solvate containing a lower alcohol whose boiling temperature is lower than that of water is used. For example, when heating an aripiprazole hemiethanolate, the heating temperature is usually around 78 to 85° C., more specifically around 79 to 82° C., and particularly around 80° C.

Fine particles of the crystals after heating treatment (drying) are the fine particles of anhydride crystals B of aripiprazole, and the volume average particle size thereof is equivalent to that of the fine particles of the wet-milled aripiprazole lower alcohol solvate. The volume average particle size is usually less than 50 μm, preferably 5 to 40 μm, more preferably 10 to 30 μm, still more preferably 10 to 25 μm, and particularly preferably 15 to 20 μm.

Fine particles of the crystals after heating treatment (drying) are the fine particles of anhydride crystals B of aripiprazole. These particles have the physicochemical properties (1) to (5) described above, and also have a low hygroscopicity; specifically, the water content thereof after 24 hours of conditioning in a desiccator adjusted to a temperature of 60° C. and a humidity of 100% is 0.4% or less, further 0.2% or less, and furthremore 0.1% or less.

3. Pharmaceutical Composition

The fine particles of aripiprazole anhydride crystals B produced by the method of the present invention are prepared into pharmaceutical compositions together with a pharmaceutically acceptable carrier.

Examples of pharmaceutically acceptable carriers include diluents, excipients, and the like, such as fillers, extenders, binders, wetting agents, disintegrating agents, surfactants, and lubricants.

The pharmaceutical composition of the present invention may have a dosage form of a general medicinal preparation. Examples include tablets, flash-melt tablets, pills, powders, liquids, suspensions, emulsions, granules, capsules, suppositories, injections (liquids, suspensions, and the like), and the like.

Specifically, the pharmaceutical composition comprising fine particles of aripiprazole anhydride crystals B, which is disclosed in Patent Literature 3, can be prepared.

EXAMPLES

Next, the present invention is described in detail with reference to a reference example and examples. However, the present invention is not limited thereto.

Reference Example 1

Potassium carbonate (8.39 g) was dissolved in water (140 mL), followed by the addition of 7-(4-chlorobutoxy)-3,4-dihydrocarbostyril (19.4 g) and 1-(2,3-dichlorophenyl)piperazine monohydrochloride (16.2 g) thereto. The mixture was refluxed under stirring for about 3 hours. After reaction, the resulting mixture was cooled, and precipitated crystals were filtered. The crystals were dissolved in ethyl acetate (350 mL), and about 210 mL of water/ethyl acetate azeotrope was distilled under reflux. The remaining solution was cooled, and precipitated crystals were filtered. The thus-obtained crystals were dried at 60° C. for 14 hours, thereby obtaining 20.4 g of crude aripiprazole (yield: 74.2%).

Example 1

Crude aripiprazole (50 g) obtained in the same manner as in Reference Example 1 was dissolved in 1,000 mL (20-fold amount) of anhydrous ethanol (concentration: 99.5%) by heating and stirring. After dissolution, the resulting mixture was cooled to 10° C. to precipitate crystals. A slurry liquid containing the resulting hemiethanolate (volume average particle size of 100 µm to 200 µm) was subjected to wet-milling. As a wet mill, CLEARMIX W-Motion produced by M Technique Co., Ltd. was used. The slurry liquid was circulated and milled at a rotor speed of 19,800 rpm and a screen speed of 17,800 rpm for 30 minutes. The volume average particle size of the crystals reached 15 µm to 20 µm in 5 minutes. Subsequently, the circulated liquid (dispersion of crystals) was subjected to solid-liquid separation, and the thus-obtained crystals were dried by heating at 80° C. for 40 hours, thereby obtaining fine particles of aripiprazole anhydride crystals B. The yield was 40 g (yield: 90%). The volume average particle size was 15 to 20 µm.

The thus-obtained fine particles of aripiprazole anhydride crystals B did not show hygroscopicity of 4% or more even after being left to stand for 24 hours in a desiccator adjusted to a temperature of 60° C. and a humidity of 100% (see Table 1).

TABLE 1

| Sample | Water content (%) at the start | Water content (%) after 24 hours |
| --- | --- | --- |
| Example 1 | 0.11 | 0.10 |

In this way, desired fine particles of aripiprazole anhydride crystals B having high purity were obtained under more moderate conditions in a short process, using the above-described method.

Example 2

Crude aripiprazole (50 g) obtained in the same manner as in Reference Example 1 was dissolved in 1,000 mL (20-fold amount) of anhydrous ethanol (concentration: 99.5%) by heating and stirring. After dissolution, the resulting mixture was cooled to 10° C. to precipitate crystals. A slurry liquid containing the resulting hemiethanolate (volume average particle size of 100 µm to 200 µm) was subjected to wet-milling using CLEARMIX Single Motion produced by M Technique Co., Ltd. The slurry liquid was circulated and milled at a rotor speed of 19,800 rpm for 30 minutes. The volume average particle size of the crystals reached 15 µm to 20 µm in 30 minutes. Subsequently, the circulated liquid (dispersion of crystals) was subjected to solid-liquid separation, and the thus-obtained crystals were dried by heating at 80° C. for 40 hours, thereby obtaining fine particles of aripiprazole anhydride crystals B. The yield was 40 g (yield: 90%). The volume average particle size was 15 to 20 µm.

The water content of the obtained crystals was 0.01%. The water content thereof after 24 hours of conditioning in a desiccator adjusted to a temperature of 60° C. and a humidity of 100% was 0.01% or less.

Example 3

Crude aripiprazole (7 g) was heated and stirred in 560 mL (80-fold amount) of methanol in a flask by heating and stirring. Methanol was added until the crude aripiprazole was dissolved. Complete dissolution was confirmed at the final amount of 700 mL (100-fold amount). Subsequently, the resulting mixture was cooled to 10° C. to precipitate crystals. A slurry liquid containing the resulting monomethanolate was transferred to a beaker and subjected to wet-milling using a homogenizer. As a homogenizer, a T.K. Robomix produced by PRIMIX Corporation was used. The slurry liquid was milled at a rotor speed of 12,000 rpm for 1 hour. At that time, the beaker was externally cooled in ice water because heat was generated. The volume average particle size of the crystals after milling was 15 µm to 26 µm in 30 minutes. The thus-obtained slurry liquid (dispersion of crystals) was subjected to solid-liquid separation, and the crystals were dried by heating at 80° C. for 40 hours, thereby obtaining fine particles of aripiprazole anhydride crystals B. The yield was 6.11 g (yield: 87.3%). The volume average particle size of the crystals was 15 µm to 22 µm.

The water content of the obtained crystals was 0.08%. The water content of the crystals after 24 hours of conditioning in a desiccator adjusted to a temperature of 60° C. and a humidity of 100% was 0.17%.

All references cited herein are incorporated herein by reference.

The invention claimed is:

1. A method for producing fine particles of aripiprazole anhydride crystals B, the method comprising the steps of:
   (a) heating and dissolving crude aripiprazole in a lower alcohol, and subsequently cooling the resulting mixture to precipitate crystals to obtain crystals of aripiprazole lower alcohol solvate;
   (b) subjecting the crystals of aripiprazole lower alcohol solvate to wet-milling in the form of a slurry containing the lower alcohol; and
   (c) subjecting the dispersion of the wet-milled crystals to solid-liquid separation to obtain the crystals, and heating the crystals.

2. The production method according to claim 1, wherein the volume average particle size of the obtained fine particles of aripiprazole anhydride crystals B is less than 50 µm.

3. The production method according to claim 1 or 2, wherein the lower alcohol is methanol or ethanol.

4. The production method according to claim 3, wherein the lower alcohol is ethanol.

5. The production method according to claim 4, wherein the lower alcohol substantially contains no water.

6. The production method according to claim 5, wherein the water content in the lower alcohol is less than 10 vol %.

7. The production method according to claim 6, wherein the volume average particle size of the wet-milled crystals in step (b) is less than 50 µm.

8. The production method according to claim 7, wherein the volume average particle size of the wet-milled crystals in step (b) is 15 to 20 µm.

9. The production method according to claim 1 or 2, wherein the heating temperature in step (c) is in the range near the boiling point of the lower alcohol to about 125° C.

10. The production method according to claim 1 or 2, wherein the lower alcohol is ethanol, and the heating temperature in step (c) is in the range of about 78 to 125° C.

* * * * *